(12) United States Patent
Amin et al.

(10) Patent No.: US 6,465,505 B1
(45) Date of Patent: Oct. 15, 2002

(54) BENZYL-SUBSTITUTED BENZIMIDAZOLES

(75) Inventors: Kosrat Amin; Mikael Dahlström, both of Mölndal; Peter Nordberg, Sävedalen; Ingemar Starke, Göteborg, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 08/875,132

(22) PCT Filed: Jun. 5, 1997

(86) PCT No.: PCT/SE97/00991

§ 371 (c)(1),
(2), (4) Date: Jul. 17, 1997

(87) PCT Pub. No.: WO97/47603

PCT Pub. Date: Dec. 18, 1997

(30) Foreign Application Priority Data

Jun. 10, 1996 (SE) ............................................ 9602286

(51) Int. Cl.[7] .................. A61K 31/4184; C07D 235/12; C07D 235/14
(52) U.S. Cl. .................. 514/394; 548/309.7; 548/310.1
(58) Field of Search ...................... 514/394; 548/309.7, 548/310.1

(56) References Cited

U.S. PATENT DOCUMENTS

| 5,106,862 A | 4/1992 | Briving et al. |
| 6,265,415 B1 | 7/2001 | Amin et al. ................ 514/300 |

FOREIGN PATENT DOCUMENTS

| EP | 266326 | 5/1988 |
| EP | 774462 | 5/1997 |
| WO | WO 96 04251 | 2/1996 |

OTHER PUBLICATIONS

Cram and Hammond, "Organic Chemistry", McGraw Hill Book Co., NY (1964) 2nd Ed., pp 565–567.*

Sachs, et al., Annu. Rev. Pharmacol. Toxicol. 35: 277–305 (1995).

* cited by examiner

Primary Examiner—Patricia L. Morris
(74) Attorney, Agent, or Firm—White & Case LLP

(57) ABSTRACT

The present invention relates to benzimidazole derivatives of the formula (I), in which the phenyl moiety is substituted with lower alkyl in 2- and 6-position, which inhibit exogenously or endogenously stimulated gastric acid secretion and thus can be used in the prevention and treatment of gastrointestinal inflammatory diseases.

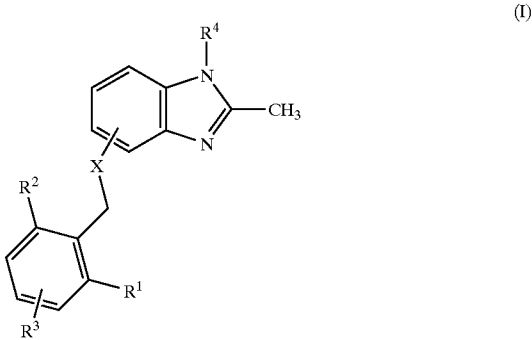

16 Claims, No Drawings

BENZYL-SUBSTITUTED BENZIMIDAZOLES

TECHNICAL FIELD

The present invention relates to novel compounds, and therapeutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a therapeutically acceptable salt thereof, as active ingredient; and to the use of the active compounds in the manufacture of medicaments for the medical use indicated above.

BACKGROUND ART

Benzimidazole derivatives of the following formula, active as anti-ulcer agents, are disclosed in EP-B-0 266 326 and in U.S. Pat. No. 5,106,862:

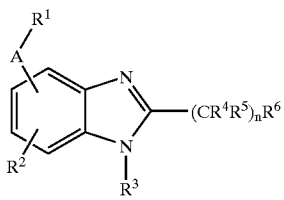

wherein $R^1$ is i.a. an aryl group of the formula:

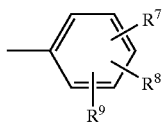

in which each of $R^7$, $R^8$ and $R^9$ independently represents i.a. H or $C_1$–$C_6$ alkyl, or halogen;

$R^2$ is i.a. H;

$R^3$ is i.a. H or $C_1$–$C_6$ alkyl;

n is an integer 0–6;

$R^4$, $R^5$ and $R^6$ are H or $C_1$–$C_6$ alkyl;

A is alkylene up to 6 carbon atoms optionally interrupted by a hetero atom such as O or N.

For a review of the pharmacology of the gastric acid pump (the $H^+$, $K^+$-ATPase), see Sachs et al. (1995) Annu. Rev. Pharmacol. Toxicol. 35: 277–305.

DISCLOSURE OF THE INVENTION

It has surprisingly been found that compounds of the Formula I, which are substituted benzimidazole derivatives in which the phenyl moiety is substituted with lower alkyl in 2- and 6-position, are particularly effective as inhibitors of the gastrointestinal $H^+$, $K^+$-ATPase and thereby as inhibitors of gastric acid secretion.

In one aspect, the invention thus relates to compounds of the general Formula I:

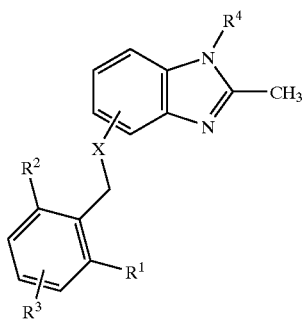

or a pharmaceutically acceptable salt thereof, wherein $R^1$ is lower alkyl;

$R^2$ is lower alkyl;

$R^3$, which is in position 3, 4, or 5 of the phenyl ring, is
  (a) H,
  (b) halogen, or
  (c) lower alkyl;

$R^4$ is
  (a) H, or
  (b) lower alkyl;

X, which is connected to the heterocycle in the position 4 or 7, is
  (a) NH, or
  (b) O.

As used herein, the term "lower alkyl" denotes a straight or branched alkyl group having from 1 to 6 carbon atoms. Examples of said lower alkyl include methyl, ethyl, n-propyl, iso-propyl, n-butyl, iso-butyl, sec-butyl, t-butyl and straight- and branched-chain pentyl and hexyl.

The term "halogen" includes fluoro, chloro, bromo and iodo.

Both pure enantiomers, racemic mixtures and unequal mixtures of two enantiomers are within the scope of the invention. It should be understood that all the diastereomeric forms possible (pure enantiomers, racemic mixtures and unequal mixtures of two enantiomers) are within the scope of the invention. Also included in the invention are derivatives of the compounds of the Formula I which have the biological function of the compounds of the Formula I.

Depending on the process conditions the end products of the Formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably therapeutically acceptable salts. Examples of such acids are hydrohalogen acids such as hydrochloric acid, sulfuric acid, phosphoric acid, nitric acid, aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, halogenbensenesulfonic acid, toluenesulfonic acid or naphthalenesulfonic acid.

Preferred compounds according to the invention are those of the formula I wherein $R^1$ is $CH_3$ or $CH_2CH_3$; $R^2$ is $CH_3$ or $CH_2CH_3$; $R^3$ is H, 4-F or 4-Cl; $R^4$ is H or $CH_3$ and X is $NH$ or O connected to the heterocycle in the 4-position.

Particularly preferred compounds according to the invention are:

4-(2,6-dimethylbenzylamino)-2-methylbenzimidazole;
4-(2,6-dimethylbenzyloxy)-2-methylbenzimidazole;
4-(2,6-dimethyl-4-fluorobenzylamino)-2-methylbenzimidazole;
4-(2,6-dimethyl-4-fluorobenzyloxy)-2-methylbenzimidazole;
4-(2,6-dimethylbenzylamino)-1,2-dimethylbenzimidazole;
4-(2-ethyl-6-methylbenzylamino)-2-methylbenzimidazole;
4-(2,6-diethylbenzylamino)-2-methylbenzimidazole;
4-(2,6-dimethyl-4-fluorobenzylamino)-1,2-dimethylbenzimidazole;
4-(2,6-dimethyl-4-fluorobenzyloxy)-1,2-dimethylbenzimidazole.

Preparation

The present invention also provides the following processes A to C for the manufacture of compounds with the general Formula I:

Process A

Process A for manufacture of compounds with the general Formula I comprises the following steps:

a) Compounds of the general Formula II

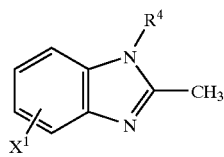

wherein $X^1$ is $NH_2$ or OH connected to the heterocycle in the position 4 or 7 and $R_4$ is as defined for Formula I, can be reacted with compounds of the general Formula III:

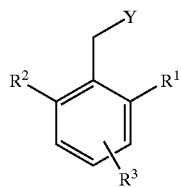

wherein $R^1$, $R^2$ and $R^3$ are as defined for Formula I and Y is a leaving group, such as a halide, tosyloxy or mesyloxy, to the compounds of the Formula I.

It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide; a sodium alcoholate, such as sodium methoxide and sodium ethoxide; an alkali metal hydride such as sodium hydride and potassium hydride; an alkali metal carbonate, such as potassium carbonate and sodium carbonate; or an organic amine, such as triethylamin.

Process B

Process B for manufacture of compounds with the general Formula I comprises the following step:

A compound of the Formula IV:

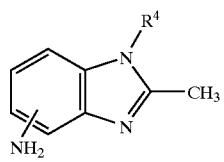

wherein $R^4$ is as defined for Formula I and the $NH_2$ group is connected to the heterocycle in the position 4 or 7, can be reacted with compounds of the general Formula V:

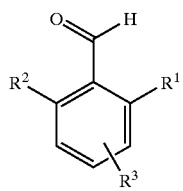

wherein $R^1$, $R^2$ and $R^3$ are as defined for Formula I, in the presence of a Lewis acid e.g. zinc chloride to the compounds of the Formula VI:

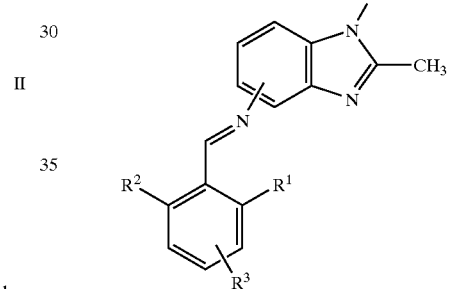

wherein $R^4$ is as defined for Formula I and the imine nitrogen is connected to the heterocycle in the position 4 or 7, whereby the compounds of the general Formula VI are reduced e.g. by using sodium borhydride or sodiumcyano borhydride to compounds of the general Formula I. The reactions can be carried out under standard conditions in an inert solvent e.g. methanol orethanol.

Process C

Compounds of the general Formula I wherein $R^4$ is "lower alkyl" can be made by alkylation of compounds of the general Formula I wherein $R^4$ is H in an inert solvent, e.g. acetonitrile or acetone, with or without base with compounds of the general Formula VII:

$R^4X^2$ VII wherein $R^4$ is as defined for Formula I and $X^2$ is a leaving group e.g. a halide, mesylate or tosylate. The base is e.g. an alkali metal hydroxide, such as sodium hydroxide and potassium hydroxide; a sodium alcoholate, such as sodium methoxide and sodium ethoxide; an alkali metal hydride such as sodium hydride and potassium hydride; an alkali metal carbonate, such as potassium carbonate and sodium carbonate; or an organic amine, such as triethylamine.

Medical Use

In a further aspect, the invention relates to compounds of the formula I for use in therapy, in particular for use against gastrointestinal inflammatory diseases. The invention also provides the use of a compound of the formula I in the manufacture of a medicament for the inhibition of gastric acid secretion, or for the treatment of gastrointestinal inflammatory diseases.

The compounds according to the invention may thus be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrome. Furthermore, the compounds may be used for treatment of other gastrointestinal disorders where gastric antisecretory effect is desirable, e.g. in patients with gastrinomas, and in patients with acute upper gastrointestinal bleeding. They may also be used in patients in intensive care situations, and pre-and postoperatively to prevent acid aspiration and stress ulceration.

Pharmaceutical Formulations

In yet a further aspect, the invention relates to pharmaceutical compositions containing at least one compound of the invention, or a therapeutically acceptable salt thereof, as active ingredient.

The compounds of the invention can also be used in formulations together with other active ingredients, e.g. antibiotics such as amoxicillin.

For clinical use,.the compounds of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

The compounds according to the invention can also be used in formulations together with other active ingredients, e.g. for the treatment or prophylaxis of conditions involving infection by *Helicobacter pylori* of human gastric mucosa. Such other active ingredients may be antimicrobial agents, in particular:

b-lactam antibiotics such as amoxicillin, ampicillin, cephalothin, cefaclor or cefixime;

macrolides such as erythromycin, or clarithromycin;

tetracyclines such as tetracycline or doxycycline;

aminoglycosides such as gentamycin, kanamycin or amikacin;

quinolones such as norfloxacin, ciprofloxacin or enoxacin;

others such as metronidazole, nitrofurantoin or chloramphenicol; or preparations containing bismuth salts such as bismuth subcitrate, bismuth subsalicylate, bismuth subcarbonate, bismuth subnitrate or bismuth subgallate.

EXAMPLES

1. PREPARATION OF COMPOUNDS OF THE INVENTION

Example 1.1

Synthesis of 4-(2,6-dimethylbenzylamino)-2-methylbenzimidazole

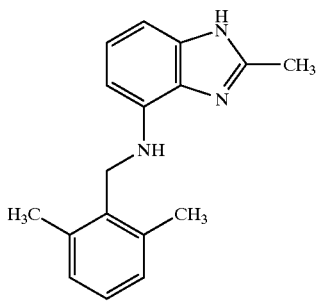

4-amino-2-methylbenzimidazole (6.0 g, 0.041 mol) was dissolved in acetonitrile (120 ml). To the solution were added 2,6-dimethylbenzylchloride (6.3 g, 0.041 mol), sodium carbonate (16 g, 0.15 mol) and a cat. amount of sodium iodide and the reaction mixture was refluxed for 3 h. The sodium carbonate was removed by filtration and was washed with methylene chloride. Vacuum evaporation of the solvent gave an oily residue which was subjected to flash chromatography on silica gel, methylene chloride: methanol (10:1). The residue was crystallized by treating with ethyl acetate to obtain 3.3 g ( 30%) of the title compound.

($^1$H-NMR, 300 MHz, CDCl$_3$): 2.35 (s, 6H), 2.50 (s, 3H), 4.35 (s, 2H), 4.45 (bs, 1H), 6.50 (d, 1H), 6.75 (d, 1H), 6.95–7.15 (m, 4H).

Example 1.2

Synthesis of 4-(2,6-dimethylbenzyloxy)-2-methylbenzimidazole

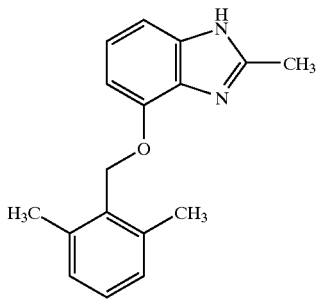

4-hydroxy-2-methylbenzimidazole (0.59 g, 4 mmol) was dissolved in acetonitrile (15 ml). To the solution were added 2,6-dimethylbenzylchloride (0.52 g, 4 mmol) and sodium hydroxide (0.16 g, 4 mmol) (dissolved in 1 ml water) and the reaction mixture was refluxed for 2 h. The solvent was evaporated under reduced pressure and the residue was dissolved in methylene chloride and was washed with 2 M NaOH. The organic layer was separated, dried over sodium sulfate and evaporated under reduced pressure. The oily residue was purified by column chromatography on silica gel. The product was eluted with methylene chloride containing 5% methanol. Crystallization from acetonitrile gave 0.18 g (18%) of the title compound.

($^1$H-NMR, 300 MHz, DMSO-d$_6$): 2.3 (s, 6H), 2.40 (s, 3H), 5.25 (s, 2H), 6.9 (d, 1H), 7.05–7.15 (m, 4H), 7.2 (t, 1H).

Example 1.3

Synthesis of 4-(2,6-dimethyl-4-fluorobenzylamino)-2-methylbenzimidazole

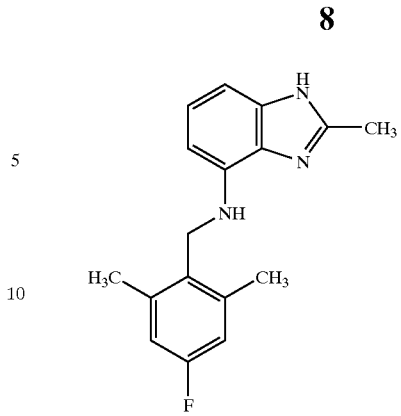

4-amino-2-methylbenzimidazole (0.6 g, 4,1 mmol) was dissolved in acetonitrile (10 ml). To the solution were added 2,6-dimethyl-4-fluoro-benzylbenzylbromide (0.89 g, 4,1 mmol) and potassium carbonate (0.68 g, 4.9 mmol) and the mixture was warmed at 70–80° C. for 3 h. The reaction mixture was cooled to room temperature and methylene chloride (25 ml) and water (25 ml) was added. The organic layer was separated, dried over sodium sulfate and was evaporated under reduced pressure. The residue was crystallized twice from ethyl acetate and was purified by column chromatography on silica gel, using methylene chloride containing 10% methanol as eluent. There was obtained 0.26 g (22%) of the title compound.

($^1$H-NMR, 300 MHz, CDCl$_3$): 2.3 (s, 6H), 2.45 (s, 3H), 4.25 (s, 2H), 4.35 (bs, 1H), 6.45 (d, 1H), 6.65 (d, 2H), 6.7 (d, 1H), 7.1 (t, 1H).

Example 1.4

Synthesis of 4-(2,6-dimethyl-4-fluorobenzyloxy)-2-methylbenzimidazole

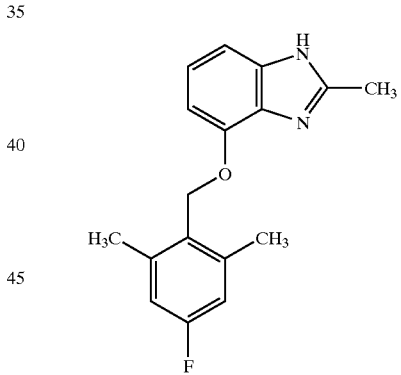

4-hydroxy -2-methylbenzimidazole (0.57 g, 3.8 mmol) was dissolved in acetonitrile (4 ml). To the solution were added sodium hydroxide (0.17 g, 43 mmol) (dissolved in 1 ml water) and 2,6-dimethyl-4-fluorobenzylbromide (0.82 g, 3.8 mmol) dissolved in acetonitrile (6 ml) and the reaction mixture was refluxed for 80 min. and was stirred for 20 h. at ambient temperature. To the reaction mixture was added methylene chloride (25 ml) and water (25 ml). The organic layer was separated, washed three times with 2 M NaOH, dried over sodium sulfate and was evaporated under reduced pressure. The residue was crystallized from ethyl acetate and was then purified twice by column chromatography on silica gel a) methylene chloride: methanol (10:1) b) ethyl acetate: methanol:acetic acid: water (96:6:6:4). There was obtained 0.066 g (6%) of the title compound.

($^1$H-NMR, 300 MHz, DMSO-d$_6$): 2.3 (s, 6H), 2.5 (s, 3H), 5.05 (s, 2H), 6.7 (d, 2H), 6.8 (d, 1H), 7.15 (t, 1H), 7.25 (d, 1H).

Example 1.5
Synthesis of 4-(2,6-dimethylbenzylamino)-1,2-dimethylbenzimidazole

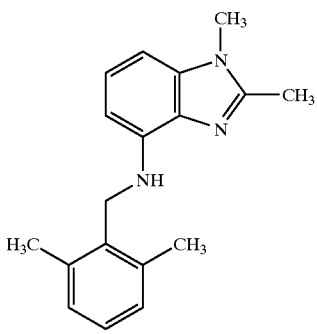

4-(2,6-dimethylbenzylamino)-2-methylbenzimidazole (0.2 g 0.75 mmol) was dissolved in acetonitrile (15 ml). To the solution were added methyl iodide (0.05 ml 0.82 mmol) and potassium carbonate (0.2 g 1.4 mmol) and the reaction mixture was stirred at ambient temperature for 20 h. The solids were removed by filtration and was washed with methylene chloride. Vacuum evaporation of the solvent gave an oily residue which was subjected to flash chromatography on silica gel, methylene chloride: methanol (10:1). Crystallization from acetonitrile gave 0.018 g (9%) of the title compound.

($^1$H-NMR, 500 MHz, CDCl$_3$): 2.4 (s, 6H), 2.55 (s, 3H), 3.65 (s, 3H), 4.4 (d, 2H), 4.55 (bs, 1H), 6.55 (d, 1H), 6.7 (d, 1H) 7.05 (d, 2H), 7.1 (t, 1H), 7.2 (t, 1H).

Example 1.6
Synthesis of 4-(2-Ethyl-6-methylbenzylamino)-2-methylbenzimidazole

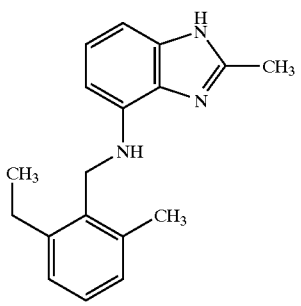

4-amino-2-methylbenzimidazole (0.4 g, 2.7 mmol) and 2-ethyl-6-methylbenzylchloride (0.46 g, 2.7 mmol) were dissolved in 10 ml dimethoxyethane. Sodium carbonate (0.5 g, 4.7 mmol) and (0.2 g, 4.7 mmol) of potassium iodide were added to the solution. The reaction mixture was refluxed to for 2 h. Inorganic salts were removed by filtration and washed with dimethoxyethane. The filtrate was evaporated to dryness. The residue was purified by column chromatography on silica gel. The product was eluted with a 50:50 mixture of methylene chloride and ethyl acetate. There was obtained 0.21 g of the title compound. ($^1$H-NMR, 400 MHz, CDCl$_3$): 1.1 (t, 3H), 2.35 (s, 3H), 2.45 (s, 3H), 2.70 (q, 2H), 4.35 (s, 2H), 4.45 (bs, 1H), 6.55 (d, 1H), 6.75 (d, 1H), 6.95–7.20 (m, 4H).

Example 1.7
Synthesis of 4-(2,6-diethylbenzylamino)-2-methylbenzimidazole

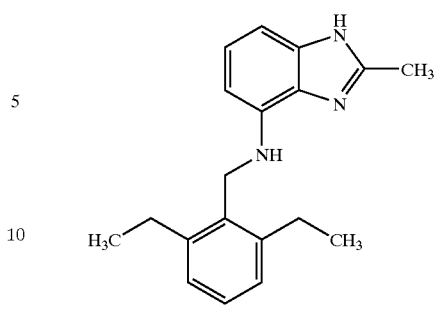

4-Amino-2-methylbenzimidazole (0.79 g, 5.4 mmol) and 2,6-diethylbenzaldehyde (1.1 g, 6.6 mmol) were dissolved in methanol (30 ml). ZnCl$_2$ (0.9 g, 6.6 mmol) and subsequently NaBH$_3$CN (0.42 g, 6.6 mmol) in small portions were added and the mixture was refluxed under argon for 3 hours and was stirred at room temperature for 16 h. The mixture was poured over an aqueous 1M NaOH solution (50 ml). The resultant yellow suspension was extracted with DCM and the organic solution was washed with brine, dried over Na$_2$SO4 and then evaporated under reduced pressure. The oily residue (1.8 g) was purified by crystallization from a mixture of ethyl acetate and acetonitrile to give 0.65 g (41%) of the title compound.

($^1$H-NMR, 300 MHz, CDCl$_3$): 1.2 (t, 6H), 2.5 (s, 3H), 2.27 (q, 4H), 4.35 (d, 2H), 4.45 (bs, 1H), 6.05 (d, 1H), 6.75 (d, 1H), 7.0–7.25 (m, 4H), 9.0 (bs, 1H).

Example 1.8
Synthesis of 4-(2,6-dimethyl-4-fluorobenzylamino)- 2,2-dimethylbenzimidazole.

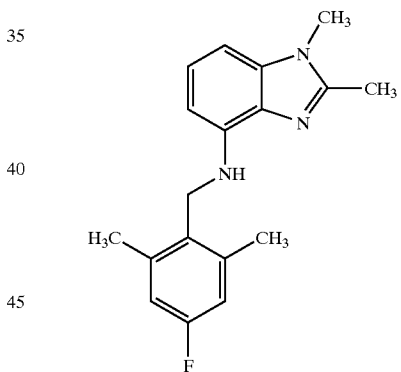

4-(2,6-Dimethyl-4-fluorobenzylamino)-2-methylbenzimidazole (0.1 g, 0.35 mmol) was dissolved in 1,2-dimethoxyethane (3 ml). Solid sodium hydroxide (25 mg, 0.63 mmol) and tetrabutylammonium bromide (5 mg, 0.016 mmol) were added. The mixture was stirred 15 minutes at ambient temperature. Methyl iodide (60 mg 0.42 mmol) was added and the reaction mixture was stirred at ambient temperature for 2.5 h. The solvent was evaporated under reduced pressure. The residue was purified by column chromatography on silica gel, using methylene chloride: ethyl acetate (50: 50) as eluent. 80 mg (76%) of the title compound was obtained.

($^1$H-NMR, 300 MHz, CDCl$_3$): 2.38 (s, 6H), 2.53 (s, 3H), 3.67 (s, 3H), 4.32 (d, 2H), 4.44 (bs, 1H), 6.51 (d, 1H), 6.68 (d, 1H), 6.75 (d, 2H), 7.18 (t, 1H).

Example 1.9
Synthesis of 4-(2,6-dimethyl4-fluorobenzyloxy)-1,2-dimethylbenzimiidazole.

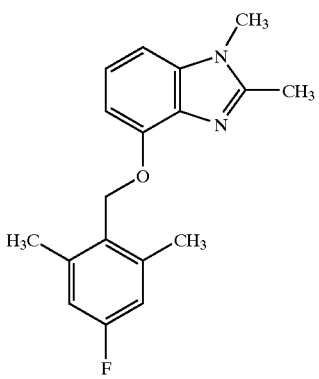

4-(2,6-dimethyl-4-fluorobenzyloxy)-2-methylbenzimidazole (180 mg, 0.63 mmol) was dissolved in 1,2-dimethoxyethane (6 ml). To the solution was added sodium hydroxide (26 mg, 0.65 mmol) and methyl iodide (0.47 ml, 0.76 mmol). The reaction mixture was stirred at ambient temperature for 3.5 h. After evaporation of the solvent, the residue was purified by chromatography on silica gel, methylene chloride: methanol 10:1. Chromatography of one of the obtained fractions on silica using ethyl acetate as eluent gave 40 mg (21%) of the title compound.

($^1$H-NMR, 300 MHz, CDCl$_3$): 2.40 (s, 6H), 2.58 (s, 3H), 3.70 (s, 3H), 5.24 (s, 2H), 6.75 (d, 2H), 6.82 (d, 1H), 6.93 (d, 1H), 7.19 (t, 1H).

Example 1.10
Preparation of the Hydrochloride Salt of 4-(2,6-dimethylbenzylamino)-2-methylbenzimidazole 4-(2,6-dimethylbenzylamino)-2-methylbenzimidazole (0.5g 1.9 mmol) was dissolved in ethyl acetate (20 ml) and methanol (6 ml). To the solution was added hydrochloric acid (12 M) (0.16 ml, 1.9 mol) and the mixture was stirred at ambient temperature for 5 min. The precipitated salt was filtered off and dried to give the desired product as a white crystalline solid (0.45 g, 79%).

($^1$H-NMR, 500 MHz, MeOD): 2.4 (s, 6H), 2.8 (s, 3H), 4.45 (s, 2H), 6.9 (d, 1H), 7.0 (d, 1H), 7.1 (d, 2H), 7.15 (t, 1H), 7.4 (t, 1H).

Example 1.11
Preparation of the Methanesulfonic Acid Salt of 4-(2,6-dimethylbenzylamino)-2-methylbenzimidazole 4-(2,6-dimethylbenzylamino)-2-methylbenzimidazole (0.5 g, 1.9 mmol) was dissolved in a etliyl acetate (20 ml) and methanol (7 ml). To the solution was added methanesulfonic acid (0.18 g, 1.9 mmol) and the mixture was stirred at ambient temperature for 5 min. The precipitated salt was filtered off and dried to give the desired product as a white crystalline solid (0.58 g, 85%).

($^1$H-NMR, 500 MHz, MeOD): 2.4 (s, 6H), 2.65 (s, 3H), 2.75 (s, 3H), 4.45 (s, 2H), 6.9 (d, 1H), 7.0 (d, 1H), 7.1 (d, 2H), 7.15 (t, 1H), 7.4 (t, 1H).

2. PREPARATION OF INTERMEDIATES

Example 2.1
Synthesis of 2,6-dimethyl-4-fluoro-benzylbromide

A mixture of 3,5-dimethyl-fluorobenzene (5 g, 0.04 mol), paraformaldehyde (15 g), hydrobromic acid (70 ml) (30% in acetic acid) and acetic acid (25 ml) was stirred at ambient temperature for 4.5 h. To the mixture were water and petroleum ether added and the organic layer was separated dried over anhydrous sodium sulfate and evaporated carefully under reduced pressure. The residue was purified by column chromatography on silica gel with petroleum ether as eluent to give the title product. (3.7 g, 43%)

($^1$H-NMR, 300 MHz, CDCl$_3$): 2.5 (s, 6H), 4.55 (s, 2H), 6.75 (d, 2H).

Example 2.2
Synthesis of 2-ethyl-6-methylbenzylchloride

2-Ethyl-6-methylbenzylalkohol (1.0 g, 6.67 mmol) was dissolved in 10 ml methylene chloride. Thionyl chloride (1.0 g, 8.5 mmol) was added. The mixture was stirred over night at ambient temperature. The reaction mixture was evaporated. The residue was dissolved in methylene chloride and filtered through 5 g of silica gel. The filtrate was evaporated. 1.0 g (89%) of the title compound (oil) was obtained.

($^1$H-NMR, 300 MHz, CDCl$_3$): 1.29 (t, 3H), 2,46 (s, 3H), 2.76 (q, 2H), 4.71 (s, 2H), 7.0–7.2 (m, 3H).

3. BIOLOGICAL TESTS

3.1. In Vitro Experiments
Acid Secretion Inhibition in Isolated Rabbit Gastric Glands Inhibiting effect on acid secretion in vitro in isolated rabbit gastric glands was measured as described by Berglindh et al. (1976) Acta Physiol. Scand. 97, 401–414.

The compounds according to Example 1.1 to 1.7 exhibited IC$_{50}$ values of less than 1.6 μM.

Compound (A) for comparison (4-benzylamino-2-methylbenzimidazole) is a compound as claimed in claim 1 of EP-B-0 266 326 wherein:

A is CH$_2$NH;

R$^2$, R$^3$, R$^4$, R$^5$ and R$^6$ are H;

n is 1; and

R$^1$ is a group of the formula II' wherein R$^7$, R$^8$ and R$^9$ are H.

Compound (A) for comparison exhibited an IC$_{50}$ value of 12.9 μM.

(A)

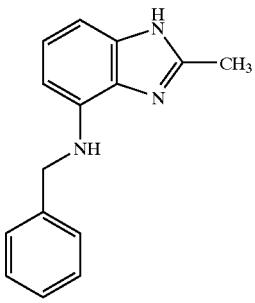

Compound (B) for comparison (4-benzyloxy-2-methyl benzimidazole) is a compound as claimed in claim 1 of EP-B-0 266 326 wherein:

A is CH$_2$O;

R$^2$, R$^3$, R$^4$, R$^5$ and R$^6$ are H;

n is 1; and

R$^1$ is a group of the formula II' wherein R$^7$, R$^8$ and R$^9$ are H.

Compound (B) for comparison exhibited an IC$_{50}$ value of 7.8 μM.

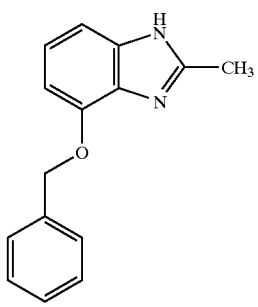

(B)

Consequently, the compounds according to the invention exhibited a significantly better inhibiting effect on acid secretion in vitro compared to the compounds (A) and (B), which carry an unsubstituted phenyl group. It is concluded that the improved effect is due to the phenyl group, in the compounds according to the invention, being substituted with lower alkyl in 2- and 6-position.

3.2. In Vivo Experiments

Inhibiting Effect on Acid Secretion in Female Rats

Female rats of the Sprague-Dawly strain were used. They were equipped with cannulated fistulae in the stomach (lumen) and the upper part of the duodenum, is for collection of gastric secretions and administration of test substances, respectively A recovery period of 14 days after surgery was allowed before testing commenced.

Before secretory tests, the animals are deprived of food but not water for 20 h. The stomach is repeatedly washed through the gastric cannula with tap water (37° C.), and 6 ml Ringer-Glucose given subcutaneously. Acid secretion is stimulated with infusion during 2.5–4 h (1.2 ml/h, subcutaneously) of pentagastrin and carbachol (20 and 110 nmol/kg.h, respectively), during which time gastric secretions are collected in 30-min fractions. Test substances or vehicle are given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4–6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.

Bioavailability in Rat

Adult rats of the Sprague-Dawley strain were used. One to three days prior to the experiments all rats were prepared by cannulation of the left carotid artery under anaesthesia. The rats used for intravenous experiments were also cannulated in the jugular vein (Popovic (1960) J. Appl. Physiol. 15, 727–728). The cannulas were exteriorized at the nape of the neck.

Blood samples (0.1–0.4 g) were drawn repeatedly from the carotid artery at intervals up to 5.5 hours after given dose. The samples were frozen until analysis of the test compound.

Bioavailability was assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, was determined by the log/linear trapezoidal rule and extrapolated to infinity by dividing the last determined blood concentration by the elimination rate constant in the terminal phase. The systemic bioavailability (F %) following intraduodenal or oral administration was calculated as F(%)=(AUC (p.o. or i.d.)/AUC (i.v.))×100.

Inhibition of Gastric Acid Secretion and Bioavailability in Conscious Dog

Labrador retriever or Harrier dogs of either sex were used. They were equipped with a duodenal fistula for the administration of test compounds or vehicle and a cannulated gastric fistula or a Heidenhaim-pouch for the collection of gastric secretion.

Before secretory tests the animals were fasted for about 18 h but water was freely allowed. Gastric acid secretion was stimulated for up to 6.5 h infusion of histamine dihydrochloride (12 ml/h) at a dose producing about 80% of the individual maximal secretory response, and gastric juice collected in consecutive 30-min fractions. Test substance or vehicle was given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples were determined by titration to pH 7.0, and the acid output calculated. The acid output in the collection periods after administration of test substance or vehicle were expressed as fractional responses, setting the acid output in the fraction preceding administration to 1.0. Percentage inhibition was calculated from fractional responses elicited by test compound and vehicle.

Blood samples for the analysis of test compound concentration in plasma were taken at intervals up to 4 h after dosing. Plasma was separated and frozen within 30 min after collection and later analyzed. The systemic bioavailability (F %) after oral or i.d. administration was calculated as described above in the rat model.

What is claimed is:

1. A compound of the Formula I:

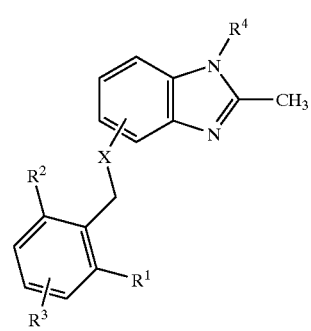

I or a pharmaceutically acceptable salt therof, wherein $R^1$ is lower alkyl;

$R^2$ is lower alkyl;

$R^3$, which is in position 3, 4, or 5 of the phenyl ring, is (a) H,
(b) halogen, or
(c) lower alkyl;

R⁴ is
(a) H, or
(b) lower alkyl;

X, which is connected to the heterocycle in the position 4 or 7, is
(a) NH, or
(b) O.

2. The compound according to claim 1, or a pharmaceutically acceptable salt thereof, wherein X is connected to the heterocycle in position 4.

3. The compound according to claim 2, or a pharmaceutically acceptable salt thereof, wherein $R^1$ is $CH_3$ or $CH_2CH_3$; $R^2$ is $CH_3$ or $CH_2CH_3$; $R^3$ is H, 4-F or 4-Cl; and $R^4$ is H or $CH_3$.

4. The compound according to claim 3 wherein the compound is 4-(2,6-dimethylbenzylamino)-2-methylbenzimidazole, or a pharmaceutically acceptable salt thereof.

5. The compound according to claim 3 wherein the compound is 4-(2,6-dimethylbenzyloxy)-2-methylbenzimidazole, or a pharmaceutically acceptable salt thereof.

6. The compound according to claim 3 wherein the compound is 4-(2,6-dimethyl-4-fluorobenzylamino)-2-methylbenzimidazole, or a pharmaceutically acceptable salt thereof.

7. The compound according to claim 3 wherein the compound is 4-(2,6-dimethyl-4-fluorobenzyloxy)-2-methylbenzimidazole, or a pharmaceutically acceptable salt thereof.

8. The compound according to claim 3 wherein the compound is 4-(2,6-dimethylbenzylamino)-1,2-dimethylbenzimidazole, or a pharmaceutically acceptable salt thereof.

9. The compound according to claim 3 wherein the compound is 4-(2-ethyl-6-methylbenzylamino)-2-methylbenzimidazole, or a pharmaceutically acceptable salt thereof.

10. The compound according to claim 3 wherein the compound is 4-(2,6-diethylbenzylamino)-2-methylbenzimidazole, or a pharmaceutically acceptable salt thereof.

11. The compound according to claim 3 wherein the compound is 4-(2,6-dimethyl-4-fluorobenzylamino)-1,2-dimethylbenzimidazole, or a pharmaceutically acceptable salt thereof.

12. The compound according to claim 3 wherein the compound is 4-(2,6-dimethyl-4-fluorobenzyloxy)-1,2-dimethylbenzimidazole, or a pharmaceutically acceptable salt thereof.

13. The compound which is a hydrochloride salt of a compound according to any one of claims 1 to 12.

14. The compound which is a methanesulfonic acid salt of a compound according to any one of claims 1 to 12.

15. A pharmaceutical formulation comprising a compound according to any one claims 1 to 12 and a pharmaceutically acceptable carrier.

16. A method for the treatment of a condition selected from the group consisting of gastric acid secretion, gastrointestinal inflammatory disease, and infection by *Hetiobacter pylori* of gastric mucosa, comprising administering to a mammal in need of such treatment an effective amount of a compound according to any one of claims 1 to 12.

* * * * *